(12) United States Patent
Klein

(10) Patent No.: US 7,348,021 B2
(45) Date of Patent: Mar. 25, 2008

(54) IMMUNOSTIMULATING COATING FOR SURGICAL DEVICES

(75) Inventor: Barbara K. Klein, North Oaks, MN (US)

(73) Assignee: Brennen Medical, LLC, St. Paul, MN (US)

(*) Notice: Subject to any disclaimer, the term of this patent is extended or adjusted under 35 U.S.C. 154(b) by 831 days.

(21) Appl. No.: 10/347,023

(22) Filed: Jan. 17, 2003

(65) Prior Publication Data

US 2003/0157143 A1 Aug. 21, 2003

Related U.S. Application Data

(63) Continuation of application No. 09/814,336, filed on Mar. 21, 2001, now Pat. No. 6,541,678, which is a continuation of application No. 09/406,551, filed on Sep. 27, 1999, now abandoned.

(51) Int. Cl.
*A61K 31/716* (2006.01)
*A61K 9/70* (2006.01)
*A61M 31/00* (2006.01)
*B32B 27/12* (2006.01)
*B32B 27/04* (2006.01)

(52) U.S. Cl. .............. 424/423; 514/54; 604/500; 424/443; 442/123

(58) Field of Classification Search .......... 424/423, 424/443; 442/123; 514/54; 604/500
See application file for complete search history.

(56) References Cited

U.S. PATENT DOCUMENTS

| | | | | |
|---|---|---|---|---|
| 4,002,173 A | * | 1/1977 | Manning et al. | 604/368 |
| 4,588,400 A | * | 5/1986 | Ring et al. | 604/304 |
| 4,851,224 A | * | 7/1989 | McAnalley | 424/744 |
| 5,143,752 A | * | 9/1992 | Nakajima et al. | 427/244 |
| 5,223,491 A | * | 6/1993 | Donzis | 514/54 |
| 5,422,340 A | * | 6/1995 | Ammann et al. | 514/12 |
| 5,885,829 A | * | 3/1999 | Mooney et al. | 435/325 |
| 5,980,918 A | * | 11/1999 | Klein | 424/401 |
| 6,168,799 B1 | * | 1/2001 | Klein | 424/401 |

* cited by examiner

*Primary Examiner*—Sharon Kennedy
(74) *Attorney, Agent, or Firm*—Moore & Hansen, PLLP

(57) ABSTRACT

The present invention discloses an immunostimulating agent that may be applied to various surgical devices to promote rapid healing and the ready acceptance and integration of the surgical devices with the body tissues at the surgical site.

4 Claims, 2 Drawing Sheets

US 7,348,021 B2

IMMUNOSTIMULATING COATING FOR SURGICAL DEVICES

CROSS REFERENCE TO RELATED APPLICATIONS

This application is a continuation of U.S. patent application Ser. No. 09/814,336 of Barbara Klein filed Mar. 21, 2001 entitled Immunostimulating Coating for Surgical Devices, now U.S. Pat. No. 6,541,678, which is a continuation of U.S. patent application Ser. No. 09/406,551, filed Sep. 27, 1999, entitled Coated Surgical Mesh, now abandoned.

FIELD OF THE INVENTION

The present invention is drawn to a coating for surgical devices that facilitates the incorporation of a surgical device into the tissues at a surgical site.

BACKGROUND OF THE INVENTION

It has become well known in the surgical arts to utilize various organic (autologous and homologous) and synthetic surgical devices at a surgical site to reinforce or augment the tissues being repaired or otherwise modified. These surgical devices include many distinct structures, including but not limited to surgical meshes, plates, screws, sutures, heart valves, bulking compounds, breast implants, and replacement joints. These devices may be fashioned from many different organic and inorganic materials.

While the functions of the aforementioned surgical devices are varied, the immunostimulating coating of the present invention acts in the same manner regardless of the type of surgical device to which it is applied. The need for a coating such as that of the present invention and the method in which it functions is generally described herein below and with more specificity as the present invention applies to a surgical mesh.

Surgical meshes are porous, gauze-like sheet materials which may be woven or spun from a variety of organic and synthetic materials. Common uses of surgical meshes include the repair of herniations and use as a structural member in gynecological surgeries. The materials from which surgical meshes are made must be biocompatible, chemically and physically inert, non-carcinogenic, mechanically strong, and easily fabricated and sterilized. Most synthetic surgical meshes are woven from monofilament or multifilament fibers to form a mesh having pores of varying sizes and geometries. Other synthetic surgical meshes are formed in a node and fibril arrangement in which the mesh is comprised of larger sections or nodes which are interconnected by fibrils of the mesh material. A non-exhaustive list of common surgical meshes is given in Table 1 below.

TABLE 1

| Chemical Component | Trade Name | Type | Pores |
| --- | --- | --- | --- |
| polypropylene | Marlex (CR Bard, Cranston, RI) | Monofilament | Irregular |
| | Prolene (Ethicon, Somerville, NJ) | Monofilament | Diamond |
| | Atrium (Atrium Medical, Hudson, NH) | Monofilament | Irregular |
| polytetrafluoroethylene PTFE | Teflon (CR Bard, Haverill, MA) | Multifilament | Circular |
| expanded PTFE | Gore-tex (WL Gore, Flagstaff, AZ) | Multifilament | Node and Fibril Macropore |
| polyethylene terephthalate | Mersilene (Ethicon, Somervill, NJ) | Multifilament | Hexagonal |
| polyglycolic acid | Dexon (absorbable) (Davis + Geck, American Cyanamid, Danbury, CT) | Multifilament | Diamond |
| Polyglactin 910 | Vicryl (absorbable) (Ethicon, Somerville, NJ) | Multifilament | Diamond |

Organic surgical meshes are typically derived from human or animal sources. Homologous surgical meshes may be derived from the tissues of a donor, from animal tissues, or from cadaveric tissues. Autologous surgical meshes are meshes that are derived from a patient's own body, and may comprise dermagraphs, fascia tissues, and dura mater.

The most common use of surgical meshes involves the reinforcement of herniations. Surgical meshes are also used in gynecological procedures including abdominal sacrocolopopexy and as suburethral slings. Other procedures which require surgical meshes include laparosopic retropubic urethropexy, intraperitoneal placement for adhesion prevention, the repair of pelvic floor hernias, rectoceles, and cystoceles. It is to be understood that the aforementioned surgical procedures do not comprise a complete list of all uses of organic and synthetic surgical meshes. New and varied uses for surgical meshes, and for all surgical devices, are being discovered on an ongoing basis and the present invention is to be construed to be applicable to all present and future uses of surgical devices such as a surgical mesh.

In many surgical procedures, it is desirable that a surgical mesh become incorporated into the tissues surrounding a surgical site. One example of such a surgical procedure is the reinforcement and repair of a herniation. In the repair of a hernia, and after the hernia has itself been closed using standard surgical techniques, a surgical mesh of appropriate size and shape is placed over the newly repaired hernia and secured in place using sutures, staples, surgical adhesives, or any other suitable connecting means. As the tissues surrounding the surgical site heal, granulation tissues growing at and around the surgical site begin to produce an extracellular matrix which, in a process called fibrosis, infiltrates and attaches to the material of the surgical mesh secured over the surgical site. Incorporation of the surgical mesh into the surgical site by the extracellular matrix strengthens the tissues at the surgical site and helps prevent re-injury.

The rate of recovery of a patient who has undergone a surgery utilizing a surgical mesh is strongly related to the rate at which the surgical mesh is incorporated into the tissues surrounding the surgical site. The rate of incorporation of the surgical mesh as well as the potential for infection and the potential for clinical complications is in turn related to the physical properties of the surgical mesh used. For example, synthetic meshes having pores or interstices of less than 10 μm in size may theoretically promote infection in that small bacteria (less than 1 μm in size) may enter the surgical site through the mesh, while important and larger macrophages and polymorphonuclear leukocytes are prevented from passing through the mesh to the surgical site. In addition, the number, size, and shape of the pores play an important role in tissue bonding to the surgical mesh. Generally, surgical meshes having larger pore sizes are difficult for fibroblasts to adhere to. Furthermore, if a surgical mesh is too stiff, it may cause continuing mechanical injury to the tissues surrounding the surgical site with which it comes into contact. In these cases, a prolonged inflammatory reaction may significantly increase patient recovery time and may also cause clinical complications such as mesh extrusion and enteric fistulas.

OBJECTS OF THE INVENTION

Because the ailments which require the use of surgical meshes are typically quite serious, recovery from surgeries undertaken to alleviate or cure these ailments can be protracted. Therefore, it is desirable to facilitate or speed up the healing and recovery process where surgical meshes are used.

Accordingly, it is an object of the present invention to provide a coating for a surgical device such as a surgical mesh that promotes the rapid incorporation and acceptance of the surgical device by the tissues surrounding the surgical site at which the surgical device has been implanted. Another object of the present invention is to stimulate the immune system to prevent surgical site infections. Yet another object of the present invention is permit the use of synthetic surgical meshes and other surgical devices that are prone to rejection by or more difficult to incorporate into the tissue surrounding a surgical site.

SUMMARY OF THE INVENTION

The present invention essentially comprises a β-D-glucan composition that is applied to a preselected surgical device. Preferably, the β-D-glucan composition is a cereal derived β-D-glucan made from one of oats, barley, or wheat, however other sources of β-D-glucan are also contemplated. Examples of other suitable sources of β-D-glucan include microbial sources such as yeast, bacteria, and fungus. A preferred embodiment of the present invention comprises a biocompatible surgical mesh that is typically used for reinforcing a surgical site. These surgical meshes may be synthetic or organic in origin. Synthetic surgical meshes are commonly made from polypropylene, polytetrafluoroethylene, expanded polytetrafluoroethylene, polyethylene terephthalate, polyglycolic acid, polyglactin, dacron-polythene reinforced silicone and polyethylene among others. Organic surgical meshes may be derived from human sources, animal sources, and cadaveric sources.

The present invention also comprises a method of promoting the acceptance of a surgical device into the tissues into which the surgical device is implanted. This method comprises the step of applying an immunostimulating agent comprising a β-D-glucan to the surgical device before implantation thereof at the surgical site.

One method of applying an imunostimulating agent such as β-D-glucan to a biocompatible surgical device comprises the steps of preparing an aqueous solution of a cereal derived β-D-glucan, immersing the pre-selected surgical device in the aqueous solution of β-D-glucan, and evaporating the water component of the aqueous solution. Alternatively, one may prepare sheets of β-D-glucan and apply these preformed sheets of β-D-glucan to a pre-selected surgical device. The sheets are formed by preparing an aqueous solution comprising a cereal derived β-D-glucan and placing the aqueous solution in a drying tray to evaporate the water component of the solution. The residue left in the drying tray is in the form of a β-D-glucan sheet. Sheets of β-D-glucan so formed are then applied to the surgical device by means of a suitable adhesive or by wetting the surgical mesh to partially dissolve the sheet of β-D-glucan.

Another method of applying a β-D-glucan to a surgical device comprises the steps of applying a suitable solvent to the surgical device and then applying a β-D-glucan powder to the wetted surface of the surgical device such that the β-D-glucan powder dissolves into the solvent to form a substantially uniform coating upon the biocompatible surgical device. Finally, the solvent is evaporated from the substantially uniform coating of β-D-glucan upon the biocompatible surgical device.

Another method of applying a immunostimulating coating to a surgical device involves spraying an aqueous solution of the immunostimulating coating onto the surgical device and then evaporating the water component of the solution to leave a suitable coating on the surface of the surgical device. The spraying method may also be used in an electrostatic spraying application that involves giving the aqueous solution being sprayed and the surgical device opposing electrostatic charges such that the aqueous solution is attracted to, and uniformly covers, the surgical device.

Vacuum deposition may also be used to apply an immunostimulating coating to a surgical device. In this application method, an aqueous solution is applied to a selected surgical device and a vacuum is subsequently drawn there around. The vacuum acts to drawn the aqueous solution tightly to the surface of the surgical device. The water component of the aqueous solution is thereafter evaporated to set the coating upon the surgical device.

The objectives and advantages of the invention will be more fully developed in the following description, made in conjunction with the accompanying drawings and wherein like reference characters refer to the same or similar parts throughout the several views.

DETAILED DESCRIPTION OF THE INVENTION

Figure 1:
FIG. 1 is an electron micrograph of a portion of an uncoated polypropylene surgical mesh that was implanted in a test animal for a duration of five days.

Although the disclosure hereof is detailed and exact to enable those skilled in the art to practice the invention, the physical embodiments herein disclosed merely exemplify the invention which may be embodied in other specific structure. While the preferred embodiment has been described, the details may be changed without departing from the invention, which is defined by the claims.

The present invention comprises an immunostimulating coating that is applied to a surgical device for the purpose of speeding recovery time of the patient. While the present invention is intended for use in humans, veterinary applications are also contemplated. The term surgical device as used herein is intended to encompass any structure or device that is intended for implantation at or to come into extended contact with a surgical site in a patient's body.

In a preferred embodiment of the present invention a pre-selected surgical mesh material, either organic or synthetic, has applied thereto a β-D-glucan composition. As used herein, the term "applied" is intended to embrace both coating and/or impregnation. Based on animal studies, it is anticipated that the addition of the β-D-glucan coating of the present invention will significantly reduce the recovery time of a patient. B-D-glucans may be derived from a number of different materials but in general, β-D-glucans are derived from cereal sources such as oats, barley and wheat or microbial sources such as bacteria, yeast, and fungi.

B-D-glucans, and especially cereal derived β-D-glucans, induce rapid differentiation of human monocytes into macrophages, the primary cell type associated with both wound healing and immunostimulation. While any β-D-glucan may be used to coat a surgical mesh in accordance with the present invention, it is preferred to utilize cereal derived β-D-glucans to coat a chosen surgical mesh.

The stimulating effect of the β-D-glucan compound helps to prevent or to fight infection at the surgical site and will promote the rapid incorporation of the surgical mesh into the tissues at the surgical site. Furthermore, surgical meshes to which tissues do not easily adhere, such as polytetrafluoroethylene (PTFE) and expanded polytetrafluoroethylene (ePTFE), may, through the increased stimulation of fibrosis made possible by the use of a β-D-glucan coating, be more successfully used in situations requiring the surgical mesh to become incorporated into the tissues surrounding the surgical site. The addition of a β-D-glucan composition to a surgical mesh will also allow the use of more flexible surgical meshes which might not otherwise be conducive to tissue incorporation or adhesion in place of more rigid surgical meshes which are more prone to causing clinical complications.

B-D-glucan coatings may also be applied to organic surgical meshes derived from autologous and homologous sources. A β-D-glucan coating will provide a smooth lubricated surface on a surgical mesh which will facilitate the surgical placement of the mesh.

Compounds classified as β-D-glucans comprise a large group of high molecular weight polymers containing glucopyranosyl units in beta-linked chains. B-D-glucans are found in essentially all living cells which are enclosed by cell walls, with considerable structural variation dependent on source. They are highly unbranched homopolysaccharides and isomerically diaposed to a α-D-glucan (e.g. starch) which is typically non-functional as a structural support component of the cell.

Figure 3:
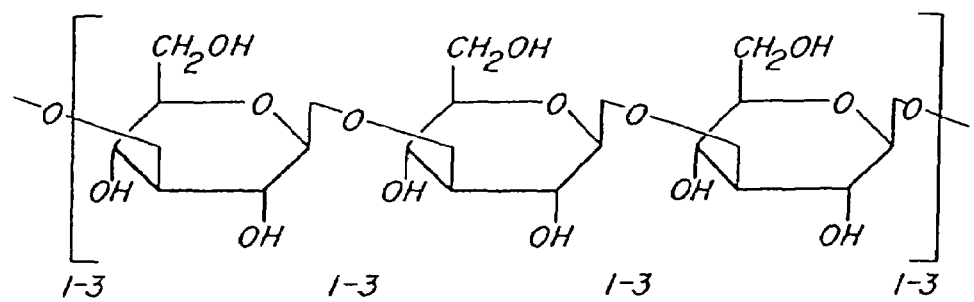
FIG. 3 is a drawing of a generalized chemical structure of a microbe-derived (1-3) β-D-glucan that may be used in the surgical mesh coating of the present invention.
Figure 4:
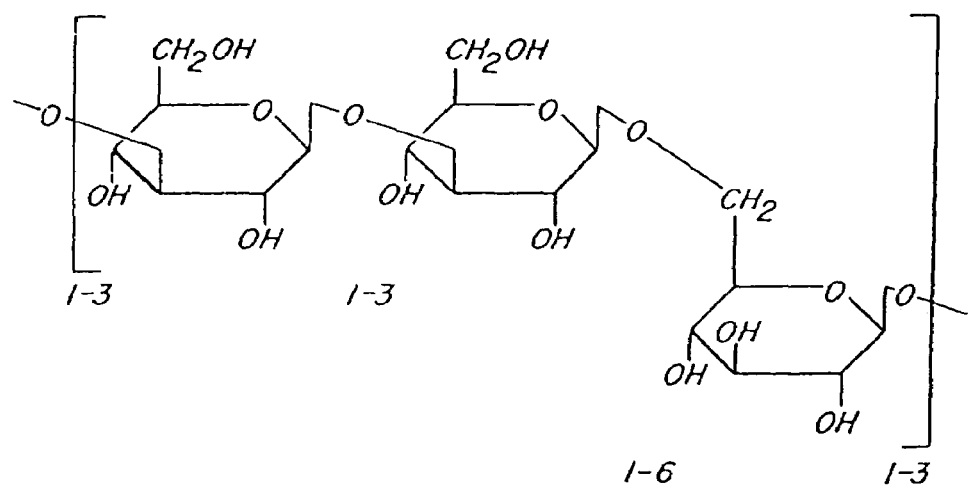
FIG. 4 is a drawing of a generalized chemical structure of a microbe-derived (1-3)(1-6) β-D-glucan that may be used in the surgical mesh coating of the present invention.

As depicted in FIG. 3, β-D-glucans derived from microbes have been generally characterized as essentially comprising (1-3)-linked chains of glucopyranosyl units. With the recent advances in test identification methods, yeast-derived glucans having primarily (1-3)-linkages with a relatively small number of (1-6)-linkages (FIG. 4) have been identified. Yeast-derived glucan polymers are often associated with mannose, and typically have a helically coiled chain shape.

Figure 5:
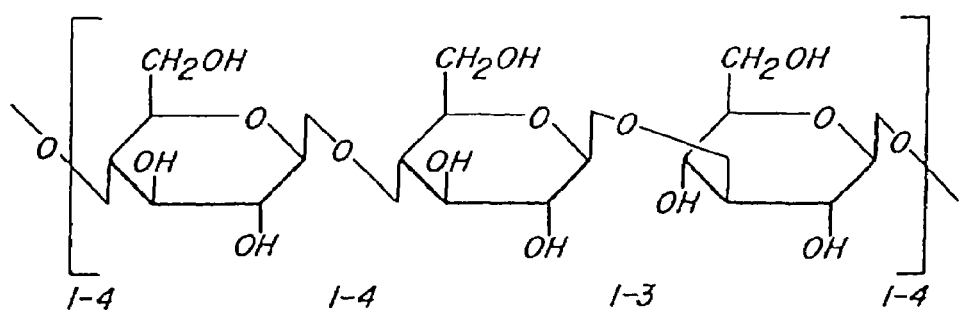
FIG. 5 is a drawing of the generalized chemical structure of mixed-linkage cereal-derived (1-3)(1-4) β-D-glucan that may be used in the surgical mesh coating of the present invention.

The mixed linkage glucan polymers found in cereals are quite different from yeast-derived and bacteria-derived polymers. Glucans derived from cereal grains such as oats, barley, and wheat, as shown in FIG. 5, have (1-3) and (1-4) linkages and generally have a linear or kinked linear chain.

Cereal-derived glucan (CDG) may be characterized as follows:

a. CDG is a long chain, unbranched polysaccharide which typically comprises about 3-4 percent of oat and barley grains. The CDG concentration is greater, e.g. 7-10 percent, in the milled bran fraction of oats.

b. CDG is found in the endosperm and aleurone cell walls of most cereal grains. The microbe-derived glucans occur in the cell wall of the yeast or bacteria.

c. CDG is a mixed-linkage molecule containing about 70 percent (1-4)-linkages and about 30 percent (1-3)-linkages. The (1-3)-linked units mostly occur singly whereas the (1-4)-linked units typically occur in groups of three or four glucopyranosyl units. Thus, the resultant structure is a series of short runs of 3 or 4 (1-4)-linked glucopyranosyl units, adjacent runs connected by (1-3) linkages. The frequencies of the groups of three (cellotriosyl) and four (cellotetraosyl)glucopyranosyl units also tend to be characteristic of the source, being affected by cereal variety, tissue age, and stage of maturity. Oat-derived CDG typically has more of the groups of three consecutive (1-4)-linked glucopyranosyl units than does barley-derived CDG. The ratio of trisaccharide to tetrasaccharide groups is about 2:1 for oats and closer to 3:1 for barley. CDG differs from microbe-derived glucans, which have all (1-3)-linkages or mostly (1-3)-linkages with some (1-6)-linkages.

d. CDG is a linear molecule, while yeast-derived glucan forms a helical shape.

e. The degree of polymerization of CDG is in the range of about 1200-1800. On the other hand, yeast-derived β-D-glucan has a much lower degree of polymerization, i.e. about 60-80. Cellulose, the primary constituent of plant cell walls, has all β (1-4) linkages and a degree of polymerization of about 10,000 to 15,000.

f. CDG forms viscous solutions in warm water. On the other hand, yeast-derived glucan is insoluble in water but dispersible in aqueous systems.

g. CDG occurs within the grain with a fairly broad range of MW, i.e. about 200,000 to 700,000. The molecular weight is believed to be dependent upon the grain species, grain source, glucan extraction conditions and particular laboratory. Microbe-derived glucan has a much lower molecular weight, in the range of about 10,000 to 14,000. Cellulose has a molecular weight of about 700,000.

h. The use of CDG as a food component has been studied extensively by various researchers; studies have included the use of CDG in regulation of glucose metabolism, hypoglycemic response, reduction in serum cholesterol, and the like.

Thus, in terms of chemical structure and molecular weight, CDG is much more like cellulose than are the microbial-derived glucans. CDG, especially that derived from oats and barley, induces rapid differentiation of human monocytes into macrophages, the primary cell type associated with both wound healing and immunostimulation.

It is to be noted that the term β-D-glucan incorporates both β-D-glucan itself and derivatives thereof. Specifically, it is often desirable to treat β-D-glucan, and particularly microbe derived β-D-glucan, so as to improve its solubility. Such treatments can alter the molecular structure of the glucan molecules, while retaining the immunostimulating properties of thereof. Accordingly, any glucan derivative that retains the desired immunostimulating properties of a β-D-glucan are to be considered within the scope of the present invention.

Preferably a β-D-glucan coating is applied to a surgical mesh by being sprayed onto the surgical mesh. Alternatively, a surgical mesh may be immersed in the β-D-glucan composition which is later dried. Other methods for applying a β-D-glucan coating to a surgical mesh include applying the β-D-glucan onto a surgical mesh using a brush or rollers or bonding a preformed sheet or film of β-D-glucan to a surgical mesh. To form a sheet or film of β-D-glucan, an aqueous solution of β-D-glucan is prepared and placed in a drying tray. β-D-glucan will, upon evaporation of the water of the aqueous solution, form a pliable sheet or film which may be glued to a pre-selected surgical mesh using a suitable adhesive. Alternatively, the β-D-glucan sheet or film may be adhered to a pre-selected surgical mesh by first wetting the mesh and then applying the β-D-glucan film to the prepared mesh.

It has also been found helpful in the application of a β-D-glucan coating to a surgical mesh to apply pressure to the surgical mesh being coated. It is preferred to completely impregnate the surgical mesh with the β-D-glucan composition. However, it may be desirable in certain situations to apply β-D-glucan compositions to only a single side of a surgical mesh. It is to be understood that a β-D-glucan coating may be applied to a surgical mesh in any manner and is not limited to the examples set forth herein.

EXAMPLE 1

A suitable polypropylene surgical mesh was obtained from Cousins Biotech, SAS, France (BIOMESH® W1). The selected surgical mesh had characteristics including a weight of 50 g/m2 and a thickness of 0.30 mm.

A 0.5 weight percent β-D-glucan (oat derived) aqueous solution was prepared. Two 10 cm×30 cm BIOMESH® W1 surgical meshes were placed in a 10 inch×15 inch drying tray in a laminar flow hood. 250 g of a β-D-glucan aqueous solution was poured into the trays with the prepared surgical meshes. Each of the surgical meshes were completely immersed in the β-D-glucan solution. The surgical meshes were then allowed to dry at 20-25° C. over a period of 48 hours. The now-coated surgical meshes were then packaged, sealed, and sterilized using commonly known procedures.

A double blind intramuscular implantation animal study was then completed according to USP XXIII and ISO 10993 procedures comparing the β-D-glucan coated surgical mesh and an identical uncoated polypropylene mesh.

After five days, the coated and uncoated surgical meshes were removed from their intramuscular implantation sites. Macroscopic observations of the respective surgical meshes showed dramatic differences between the two biopsies. The uncoated surgical mesh was relatively clear of ingrown fibrous tissues and was very easily removed from the surrounding tissue by simply pulling on the surgical mesh. Conversely, the β-D-glucan coated surgical mesh was difficult to distinguish from the surrounding tissue at the biopsy site and was difficult to remove. The β-D-glucan coated surgical mesh showed substantial integration of the surrounding tissue whereas the uncoated mesh was still relatively unincorporated.

Figure 2:
FIG. 2 is an electron micrograph of a portion of a β-D-glucan coated polypropylene surgical mesh that was implanted in a test animal for a duration of five days.

FIG. 1 is an electron micrograph of a portion of the uncoated surgical mesh after being implanted for a duration of five days. The magnification of FIG. 1 is approximately 250x. As can be seen in FIG. 1, incorporation of the uncoated surgical mesh by an extracellular matrix has only begun. The fibers of the uncoated polypropylene surgical mesh are clearly visible. Referring next to FIG. 2 which is an electron micrograph of a portion of the β-D-glucan coated polypropylene surgical mesh after a duration of five days, it can be seen that considerable colonization by fibrous tissue has taken place within the coated surgical mesh. In FIG. 2, the coated surgical mesh itself is not clearly visible and is extensively covered by a new extracellular matrix.

The benefits of rapid integration into and acceptance by the tissue at a surgical site are also very important to the success of surgically implantable devices and structures other than surgical meshes. In addition to its use as a coating for an implantable surgical mesh as described above, β-D-glucan has proven efficacious as a coating for a variety of surgically implantable device and structures including coronary appliances such as stents, pacemakers, and leads for pacemakers; on tissue augmentation devices such as breast implants and bulking agents used in cosmetic surgery and incontinence remediation procedures; on reconstruction materials such as nasal reconstruction materials and structural supports such as screws, plates, pins, artificial joints, dental implants and sutures, and on other devices and structures of similar type.

Surgically implantable devices and structures that will benefit from a coating of β-D-glucan are fashioned from myriad substances, both artificial and organic, including but not limited to polyester, polypropylene, polyethylene, polyurethane, polyolefin, polyvinyl chloride, silk, elastin, keratin, cartilage, ceramics, polytetrafluoroethylene, rayon, gortex, cellulose, collagen matrix, silicone, metals such as titanium, gold, silver and the like, metallic alloys such as stainless steel and the like, carbon in the form of graphite, diamond and the like, and various forms of carbon or other exotic composites.

A β-D-glucan coating may be applied to an implantable surgical device in much the same manner as β-D-glucan is applied to a surgical mesh. A necessarily incomplete listing of typical coating procedures is set forth hereinbelow.

For implantable surgical devices that are thin and porous such as wound dressings and surgical meshes, tray drying is an appropriate means for coating such an object with the β-D-glucan. In tray drawing, the implantable device is submerged in a shallow tray filled with a suitable β-D-glucan solution. A predetermined percentage of the water in the β-D-glucan solution is then evaporated through air or oven drying, thereby leaving the surgical device coated with the β-D-glucan. Surgical devices such as wound dressings and surgical meshes may also be dipped into a β-D-glucan solution. In applying a β-D-glucan solution to a surgical device in this manner, the surgical device is submersed in a solution of a β-D-glucan and subsequently dried either by air drying or oven drying. This process can be repeated to obtain a desired thickness or uniformity of the coating on the surgical device.

Where a surgical device is not easily submerged in a β-D-glucan solution, it may be necessary to apply the β-D-glucan coating in the form of a powder. Powder application of a β-D-glucan coating begins by wetting the surgical device with water or another suitable solvent. The powdered β-D-glucan is then applied to the surface. As the water or other solvent evaporates, the glucan remains bound to the surface of the surgical device.

As indicated above, a sheet of glucan may also be applied directly to a surgical device using water or another solvent as an adhesive whereby heat bonding or by pressing the β-D-glucan sheet into bonding contact with the surgical device. This method is especially useful in applying β-D- glucan to wound dressings and to surgical meshes and to other surgical devices that may be laid flat.

Another method for applying β-D-glucan to a surgical device is to simply use a brush or foam pad to apply a solution of β-D-glucan to the surgical device. As can be appreciated, brush application of a β-D-glucan coating to a surgical device is very akin to painting the surgical device with the β-D-glucan solution.

Spraying a coating of β-D-glucan onto a surgical device is especially useful where the surgical device has a complex surface or it is necessary to process high numbers of the surgical devices in a production run. In spray coating applications, the surgical devices may be placed on a flat surface or on a vertically oriented rack and then sprayed with the β-D-glucan solution. Surgical devices supported on a vertically oriented rack are typically sprayed over their entire surface in one step. Surgical devices that are sprayed on a flat surface may have to be turned in order to spray the remaining surface of the surgical device. Another means for spray coating surgical devices with a β-D-glucan solution involves the use of a typical tablet coating machine commonly used in the pharmaceutical industry. Once a spray coating of β-D-glucan has been applied to a surgical device, the β-D-glucan coating will be dried by air drying or oven drying.

A type of β-D-glucan application that is especially well suited to high volume processing of surgical devices is the electrostatic application of the β-D-glucan to the surgical devices. In this type of application, the surgical devices to be coated are placed in contact with an electrostatically charged supporting structure such as a metal table or a vertically oriented metal rack. A spray head for spraying the β-D-glucan solution onto the surgical devices is electrostatically charged in opposition to the charge applied to the surgical devices by its supporting structure. In this way, the charged particles of the β-D-glucan coating solution will be electrostatically attracted to the charged surgical devices. Subsequent to coating, the β-D-glucan solution is typically dried by air drying or oven drying.

Where it is desirable to impregnate the surface pores of a surgical device with the β-D-glucan coating, vacuum integration may be the desired means for applying the coating. Vacuum integration of a β-D-glucan solution into the surface of a surgical device involves submerging or otherwise covering the surgical device with the β-D-glucan solution and applying a vacuum around the surgical device so as to force the β-D-glucan solution into any pores or other irregularities in the surface of the surgical device. Subsequent to application it is preferable to dry the applied β-D-glucan coating by air or oven drying.

An exemplary embodiment of the present invention involves the coating of a breast implant with a β-D-glucan solution. In coating the breast implant, a two percent solution of β-D-glucan in the water was first prepared. The breast implant was then placed in a ring-shaped dipper. The breast implant was then dipped into the β-D-glucan solution using the dipper, and after a predetermined amount of time removed therefrom. Because of the nature of the breast implant, the β-D-glucan solution was then allowed to air dry under controlled conditions. Once the β-D-glucan solution was dry, the breast implant was removed from the dipper and packaged according to standard procedures.

Another example of the present invention involves the coating of surgical screws commonly used in orthopedic applications. In coating the surgical screws, a one percent solution of β-D-glucan and water was first prepared. The one percent solution of β-D-glucan was then placed in a spray container. The surgical screws were then placed on a drying screen and sprayed with the glucan solution, allowing the excess glucan solution to be collected below the screen. A drying screen having the now coated surgical screws thereon was then moved to a drying area to allow the screws to air dry. Once dry, the screws were removed from the drying screen and packaged for use.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without exceeding the broad scope of the invention, which is defined by the claims.

What is claimed is:

1. A surgical mesh structure providing post-operative reinforcement for organic tissue adjacent to the surgical mesh structure proximate a surgical implantation site, the surgical mesh structure comprising:
   a surgical mesh adapted to be implanted adjacent to the organic tissue proximate the surgical implantation site; wherein the surgical mesh when implanted has a coating of beta-D-glucan and the coating of beta-D-glucan promotes rapid incorporation and acceptance of the surgical mesh into the organic tissue in vivo, such that the surgical mesh becomes a part of a matrix for tissue ingrowth, thus providing the post-operative reinforcement for the organic tissue.

2. A method of forming post-operative, reinforced organic tissue at a surgical site, the surgical site including organic tissue, the method comprising the steps of:
   providing a surgical mesh having a coating of beta-D-glucan;
   implanting the surgical mesh adjacent to the organic tissue; and
   allowing the organic tissue to grow into the surgical mesh in vivo; whereby the coating of beta-D-glucan promotes rapid incorporation and acceptance of the surgical mesh into the organic tissue, thus reinforcing the organic tissue.

3. A method of forming post-operative reinforced organic tissue at a surgical site, the surgical site including organic tissue, the method comprising the steps of:
   providing a surgical mesh having a coating of beta-D-glucan; and
   implanting the surgical mesh adjacent to the organic tissue; wherein the coating of beta-D-glucan promotes rapid incorporation and acceptance of the surgical mesh into the organic tissue post-operatively to form the reinforced organic tissue in vivo.

4. A method of forming post-operative reinforced organic tissue at a surgical site, the surgical site including organic tissue, the method comprising the steps of:
   providing a surgical mesh having a coating of beta-D-glucan;
   implanting the surgical mesh adjacent to the organic tissue; and
   allowing the organic tissue to grow into the surgical mesh, thus providing the reinforced organic tissue in vivo.

* * * * *